US005298692A

United States Patent [19]

Ikeda et al.

[11] Patent Number: 5,298,692

[45] Date of Patent: Mar. 29, 1994

[54] EARPIECE FOR INSERTION IN AN EAR CANAL, AND AN EARPHONE, MICROPHONE, AND EARPHONE/-MICROPHONE COMBINATION COMPRISING THE SAME

[75] Inventors: Yasuo Ikeda; Yoshiuki Magara, both of Hiratsuka, Japan

[73] Assignee: Kabushiki Kaisha Pilot, Tokyo, Japan

[21] Appl. No.: 787,225

[22] Filed: Nov. 4, 1991

[30] Foreign Application Priority Data

Nov. 9, 1990 [JP] Japan .................................. 2-305836
Apr. 5, 1991 [JP] Japan .................................. 3-102037

[51] Int. Cl.[5] .......................... A61B 7/02; H04R 25/00

[52] U.S. Cl. .................................... 181/135; 181/137; 381/68.6; 381/69

[58] Field of Search ............... 181/126, 128, 129, 130, 181/134, 135, 137; 381/68.6, 68.7, 68.3, 69, 169, 183, 187, 188, 205

[56] References Cited

U.S. PATENT DOCUMENTS 4,498,461 2/1985 Hakansson .......................... 181/126
4,864,610 9/1989 Stevens ........................... 181/135 X
4,975,967 12/1990 Rasmussen ....................... 181/135 X
5,031,219 7/1991 Ward et al. ........................ 381/68.6
5,142,587 8/1992 Kobayashi ...................... 181/128 X

FOREIGN PATENT DOCUMENTS 57-76993 of 0000 Japan .

*Primary Examiner*—Michael L. Gellner
*Assistant Examiner*—Khanh Dang
*Attorney, Agent, or Firm*—Ladas & Parry

[57] ABSTRACT

An earpiece for insertion in an ear canal as a part of an earphone, an ear mounted microphone, an earphone/-microphone combination or the like. The earpiece comprises a body part suitable for housing an earphone transducer and/or a solid vibration pickup, and a canal insert joined to the body part. Having a generally elongate shape, the canal insert has a rear portion joined directly to the body part, a front portion away from the body part, and a midportion through which the rear and the front portions are joined together. The front portion and midportion of the canal insert have their cross sectional dimensions determined in a predefined relationship to fit as closely as feasible in the ear canals of a majority of people. The earpiece may be provided with a stabilizer, as in the form of a contact piece or pieces projecting laterally therefrom, for greater stability against dislodgement from the ear canal or rotational displacement therein. There are also disclosed herein earphones, microphones, and earphone/microphone combinations including the earpiece.

23 Claims, 8 Drawing Sheets

EARPIECE FOR INSERTION IN AN EAR CANAL, AND AN EARPHONE, MICROPHONE, AND EARPHONE/-MICROPHONE COMBINATION COMPRISING THE SAME

BACKGROUND OF THE INVENTION

This invention relates to an earpiece of novel design for insertion in an ear canal (external acoustic meatus) as a part of an earphone, an ear mounted microphone, an earphone/microphone combination or the like. The present invention is also directed to an earphone, an ear mounted microphone, and an earphone/microphone combination incorporating the earpiece as an essential component.

Japanese Unexamined Patent Publication No. 57-76993 is hereby cited as teaching earpieces explicitly designed for insertion in an ear canal as a part of an earphone or the like. One of these prior art earpieces has a canal insert of approximately cylindrical shape. The earpiece of this known shape is objectionable because the part of the ear canal in the neighborhood of its outer end, which is to receive the earpiece, varies in shape and size from one person to another. The earpiece of simple cylindrical shape can therefore be hardly expected to fit closely in the outer opening of the ear against the possibility of accidental detachment therefrom or angular displacement therein.

The Japanese unexamined patent referred to above also suggests an earpiece shaped to fit in the outer ear opening by taking advantage of the tragus, antitragus and concha of the outer ear structure. There are, however, many people who have hardly any prominent antitragus, so that this second known earpiece hardly lends itself to use with such people.

SUMMARY OF THE INVENTION

It is therefore an object of the present invention to provide an earpiece of improved shape which fits closely in the ear canal of almost any people without the likelihood of accidental detachment therefrom or angular displacement therein, which does not give pain to the wearer, and which is readily withdrawable from the ear canal.

Another object of the present invention is to provide an earphone, an ear mounted microphone, and an earphone/microphone combination, all well designed to make most effective use of the earpiece of the above improved contours.

Still another object of the present invention is to provide such an earphone, ear mounted microphone, and earphone/microphone combination that can be readily mounted to either the right or the left ear.

Stated briefly, the earpiece according to the present invention comprises a body part, and a canal insert joined to the body part for insertion in an ear canal. The canal insert is generally elongate in shape, comprising a rear portion joined directly to the body part, a front portion away from the body part, and a midportion intermediate the rear portion and the front portion. The canal insert is of substantially bilaterally symmetrical shape with respect to a median plane containing the longitudinal direction of the canal insert. Further, taken cross sectionally along planes perpendicular to the median plane, the front portion and midportion of the canal insert have dimensions that have a predetermined relationship to be set forth in the course of the following detailed description.

The earpiece contoured as above summarized fits closely in the ear canals of a greater majority of people. Generally, the ear canal has a sharp turn created midway between its exterior and interior ends by a prominent part of the wall defining the canal, as will be later explained in more detail with reference to the drawing attached hereto. The midportion of the canal insert is concaved to receive the prominent part of the canal wall. Further, as the front portion of the canal insert is received in the canal section located interiorly of the prominent part, the earpiece as a whole is positively retained in the ear canal against accidental detachment therefrom. The rotational displacement of the earpiece within the canal is effectively prevented as the earpiece is held against the tragus.

Optionally, for greater stability of the earpiece in the ear canal, particularly against rotational displacement therein, the earpiece of the above configuration may be provided with a stabilizer. The stabilizer takes the form of a contact piece or pieces adjustably mounted to the earpiece on either or both sides of its median plane. The contact piece may be so positioned on the earpiece as to butt against that part of the external ear which defines the concha. The shape and size of the contact piece may be determined so as to assure its contact with the required part of the ear under some pressure. A pair of such contact pieces may be provided for use of the earpiece with either of the right and the left ear, or only one such contact piece may be provided for use of the earpiece with only one of the ears.

The present invention is also directed to an earphone, an ear mounted microphone, and an earphone/microphone combination including the earpiece of the foregoing configuration, with or without the earpiece stabilizer. For use of the earpiece as an earphone, an earphone transducer of any known or suitable design may be housed in the earpiece, usually in its body part, with a sound channel formed through the canal insert. However, if an earphone transducer intended for use with the earpiece is too large to be housed therein, then that transducer may be provided external to the earpiece and acoustically coupled thereto.

An ear mounted microphone including the earpiece may have a microphone transducer in the form of a solid vibration pickup of known construction housed in the earpiece. The solid vibration pickup will convert into an electric signal the wearer's voice that has been transmitted thereto by bone conduction. An alternate construction is possible in which a microphone assembly is coupled to the earpiece. The microphone assembly includes a microphone transducer held close to the wearer's mouth by being supported on one end of an elongate sidepiece coupled to the earpiece.

An earphone/microphone transducer including the earpiece comprises both an earphone transducer and a microphone transducer. Normally, the earphone transducer may be housed in the earpiece. The microphone transducer may either be the noted solid vibration pickup, also housed in the earpiece, or form a part of the noted microphone assembly external to the earpiece.

It is desirable that the earphone/microphone combination of the type having the external microphone assembly be readily mountable to either the right or the left ear, rather than to one of the ears only. In order to make this possible, the earpiece and the microphone assembly may be interconnected via a rotary coupling whereby the earpiece may be turned through a predetermined angle relative to the microphone assembly.

The above objects, features and advantages of the present invention and the manner of attaining them will become more apparent, and the invention itself will best be understood, from a study of the following description and appended claims, with reference had to the attached drawings.

DESCRIPTION OF THE PREFERRED EMBODIMENTS

Figure 1:
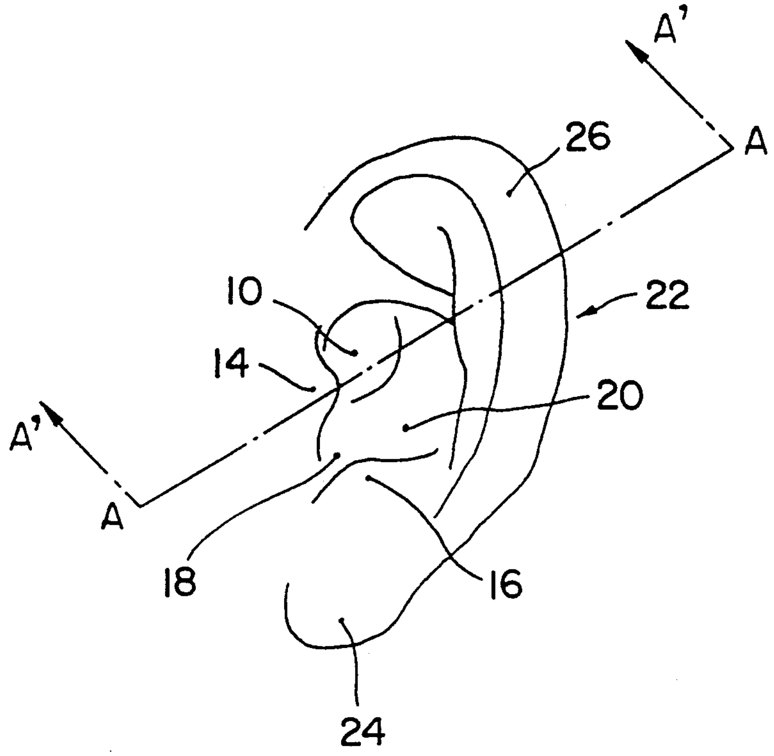
FIG. 1 is a side elevation of the left external ear of man.

It will redound to the full appreciation of the advantages of the present invention to first briefly inspect the structure of the external ear of man. With reference therefore to FIG. 1 the human ear has a canal 10 located approximately centrally, as seen in a side view as in this figure, and extending inwardly to a tympanum or eardrum membrane shown at 12 in FIG. 2. Located in front of the outer end of the canal 10 is a tragus 14 protruding posteriorly. A generally less prominent antitragus 16 protrudes upwardly from just under the outer end of the canal 10, with an incisura or notch 18 between tragus 14 and antitragus 16. A concha 20, the largest and deepest concavity of the external ear, communicates with the ear canal 10. The reference numeral 22 generally denotes the pinna, a cartilageous appendage projecting from the ear. The pinna 22 includes a pendant lobe 24 and a helix 26 joined to the earlobe and forming the incurved rim of the pinna.

Figure 2:
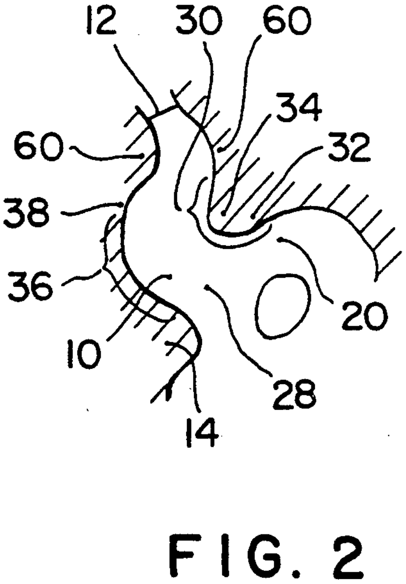
FIG. 2 is a longitudinal section through the left ear canal, taken along a plane containing the line A—A and extending in the direction of the arrows A' in FIG. 1.

A survey made by the applicant on the ears of many people revealed the variegated, intricate shapes of the ear canals. FIG. 2 is a sectional illustration of a typical left ear canal. The section is taken along a plane that contains a line A—A, FIG. 1, connecting the geometrical center of the outer end of the ear canal and the nose or the chin and which extends in the direction of the arrows A' through the glabella, the midpoint between the eyebrows.

As will be noted from FIG. 2, the bottom of the concha 20 lies opposite the tragus 14 across the outer end 28 of the canal 10. The canal meanders from the outer end 28 to the eardrum 12, with a prominence 30 creating a sharp turn in the middle of the canal. At the bottom of the concha 20, part of the skull 32 lies just below a relatively thin skin and other structures. The tip 34 of the prominence 30, although not very hard, is nevertheless harder than the tragus 14 because of the thin skin structure covering the prominence.

A gently concaved surface portion 36 extends from behind the tragus 14 toward the eardrum 12, but a small cavity 38 exists just beyond the concave surface portion 36. Beyond the cavity 38 the canal 10 is slightly bent to the left, as viewed in FIG. 2, and somewhat tapers toward the eardrum 12. The surface bounding the cavity 38 is acutely sensitive to pain, so that pushing against this surface by an earpiece should be avoided by any means. No other parts of the external ear are nearly so sensitive to pain, however.

The earpiece according to the present invention is well calculated to fit closely in the ear canal of the intricate configuration studied above. Particularly, it takes advantage of the relatively hard prominence 30, which forms as aforesaid a sharp turn in the middle of the ear canal, for positively holding the earpiece therein.

Earpiece of FIGS. 3–6

Figure 3:
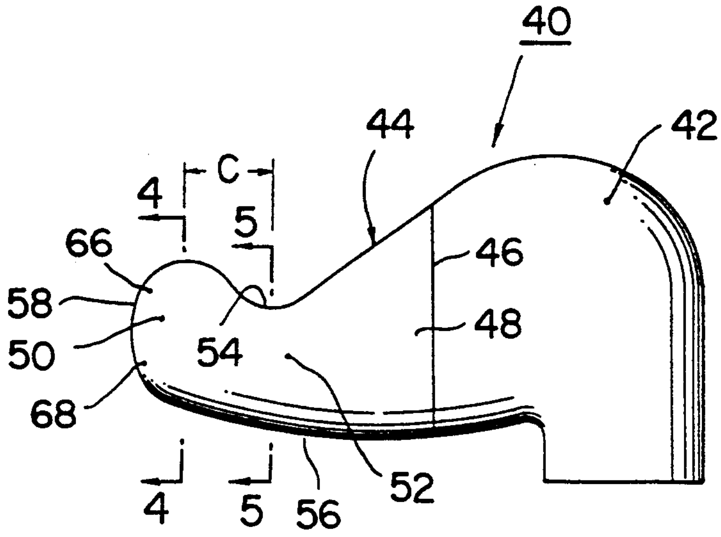
FIG. 3 is a side elevation of the earpiece contoured in accordance with the principles of the present invention.

The reader's attention is now invited to FIG. 3 for a consideration of the earpiece 40 illustrated therein by way of a typical embodiment of the present invention. The representative earpiece 40 is shown divided into a body part 42 and a canal insert 44 along a joint 46, although the earpiece could be of one piece construction. Generally in the shape of a short, L shaped tube or cylinder, the body part 42 houses electrical components to be set forth subsequently.

The canal insert 44, which, as the name implies, is intended for insertion in an ear canal, is elongate in shape, more or less circular in cross section, and is generally contoured in conformity with the ear canal configuration. The shape of the canal insert 44 may be best understood by notionally dividing it into three parts: a rear portion 48 next to the body part 42, a front portion 50 away from the body part, and a midportion 52 through which the front and rear portions are joined together. Coupled to the body part 42 so as to provide a smooth, unbroken surface continuity, the rear portion 48 tapers forwardly therefrom.

Figure 4:
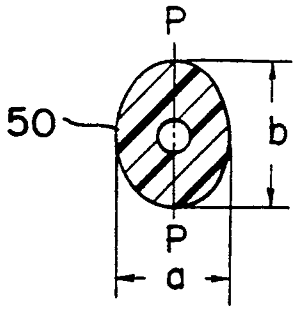
FIG. 4 is a cross section through the earpiece, taken along the line 4—4 in FIG. 3.
Figure 5:
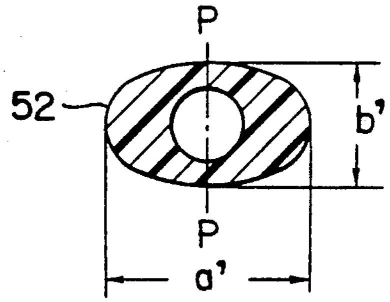
FIG. 5 is also a cross section through the earpiece, taken along the line 5—5 in FIG. 3.

FIGS. 4 and 5 are cross sectional illustrations of the front portion 50 and midportion 52, respectively, of the canal insert 44. As will be noted from these figures, the canal insert 44 is substantially of bilateral symmetry with respect to a median plane P—P. Both front portion 50 and midportion 52 are shown to be elliptical in cross sectional shape. The front portion 50 is shown elongated in a direction along the median plane P—P whereas the midportion 52 is shown elongated in a direction perpendicular to the median plane. The dimensional specifications of the front portion 50 and midportion 52, which constitute a feature of the present invention, will be set forth later in this specification.

A reconsideration of FIG. 3, which is equivalent to the sectional representation of the earpiece 40 along the median plane P—P, will indicate that the top side 54, as seen in this figure, of the canal insert 44 is relatively sharply concaved, particularly at the midportion 52. The bottom side 56, on the other hand, of the canal insert is gently convexed. The extreme tip 58 of the front portion 50 is rounded.

Figure 6:
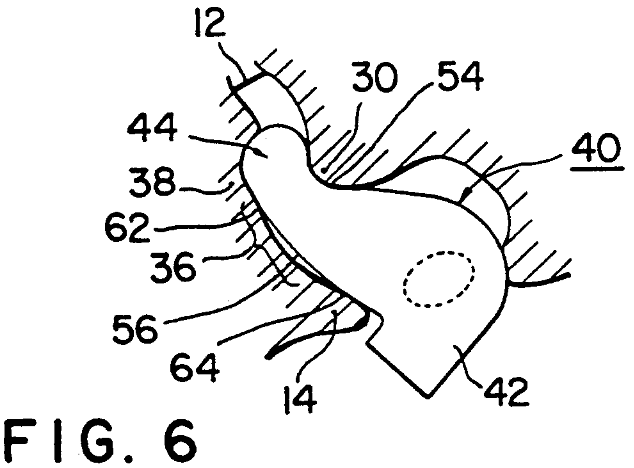
FIG. 6 is a sectional illustration of the left ear canal similar to FIG. 2 but shown together with the earpiece inserted therein and held in position.

In FIG. 6 is shown the earpiece 40 of the above configuration as inserted in an ear canal. The ear canal in this figure is shown sectioned along the same plane as in FIG. 2. It will be seen that the concavity 54 in the canal insert 44 of the earpiece 40 closely conforms to the shape of the prominence 30 within the ear canal. The front portion 50 of the canal insert is received in the space inside the prominence 30. The gentle convexity 56 of the canal insert is held against the matchingly concave surface portion 36 of the ear canal opposite the prominence 30. It will therefore be appreciated that the earpiece 40 is contoured to fit closely in the ear canal. With the earpiece 40 thus mounted in position in the ear canal, the median plane P—P of the earpiece agrees with the noted notional plane which has been set forth with reference to FIG. 1 and along which the section of the ear canal shown in both FIGS. 2 and 6 is taken.

The ear canals of a greater majority of people are elliptical in cross sectional shape at the portion just inward of the prominence 30. Further, at 60, FIG. 2, farther inward of the prominence, the ear canal is somewhat twisted and bent toward the eardrum 12. The earpiece 40 will not easily withdraw from the ear canal as its front portion 50, which may be of elliptical cross sectional shape as shown in FIG. 4, is caught in the canal space inward of the prominence 30.

An additional pronounced functional advantage of the earpiece 40 is its stability against external forces tending to cause the rotational displacement of the earpiece within the ear canal. This stability is due largely to the fact that parts 62 and 64, FIG. 6, of the convexity 56 of the canal insert 44 are closely held against the canal wall portion including the tragus 14.

As has been set forth with reference to FIG. 2, the illustrated shape of the ear canal is more or less common to all human beings. Further, even though the dimensions of the various parts of the ear canal are subject to change from one individual to another, all parts of the ear canal but the prominence 30 and the opposed concave portion 36 are sufficiently pliant to conform to the shape of the canal insert 44. The earpiece 40 according to the invention will therefore fit in the ear canal of almost any individual against accidental dislodgement or angular displacement in the face of the movements of the head of the wearer.

It has also been mentioned in connection with FIG. 2 that the ear canal surface portion defining the small cavity 38 near the eardrum 12 is very sensitive to pain. Experiment has proved that the wearer of the earpiece 40 feels little or no pain. This is presumably because the canal insert 44 of the earpiece is positively caught in the sharp curve of the canal between the prominence 30 and the opposed concave portion 36 without being pushed toward the cavity 38.

Generally, the earpiece 40 should be relatively hard and have a suitable coefficient of friction. A preferred material meeting these requirements is rigid silicone rubber. However, because of the high adaptability of the ear canal discussed above, a variety of plastics may be employed as well, either singly or in combinations of two or more. It is also possible to use different materials for different parts of the earpiece, with a view to the enhancement of comfort of the wearer. As desired, the canal insert 44 may be enlarged in the neighborhood of the line A—A, FIG. 1, in order to provide a better seal against external noise.

The applicant has carried out extensive experimentation for the determination of some pertinent dimensions of the front portion 50 and midportion 52 of the canal insert 44. It has consequently proved that the earpieces dimensioned as in the following fit in the ears of sixty percent of men and women:

$a = 6.0$ millimeters $b = 7.0$ millimeters $a' = 9.0$ millimeters $b' = 6.5$ millimeters where

- a = the cross sectional dimension of the front portion 50 of the canal insert 44 as measured in a first direction which is perpendicular to the median plane P—P (FIG. 4)
- b = the cross sectional dimension of the front portion 50 of the canal insert 44 as measured in a second direction which is contained in the median plane P—P and which is at right angles with the noted first direction
- a' = the cross sectional dimension of the midportion 52 of the canal insert 44 as measured in the noted first direction (FIG. 5)
- b' = the cross sectional dimension of the midportion 52 of the canal insert 44 as measured in the noted second direction (FIG. 5).

Let K be the ratio b/a, and K' the ratio b'/a'. Then $$K = b/a = 1.17$$

$$K' = b'/a' = 0.72$$

Therefore,

K>K'.

With this condition satisfied, the dimension c in FIG. 3 (center to center distance between front portion 50 and the midportion 52) should be from four to six millimeters.

There are, however, some people for whom the earpieces of the foregoing dimensions are too large. The following dimensions are recommended for such people:

a=6.0 millimeters b=6.0 millimeters a'=8.0 millimeters b'=6.0 millimeters c=3–4 millimeters.

Therefore, $K=b/a=1.00$ $K'=b'/a'=0.75.$

Accordingly,

K>K'.

It has also proved that earpieces of the following dimensions better suit a very small percentage of people:

a=5.5 millimeters b=5.0 millimeters a'=7.0 millimeters b'=6.3 millimeters c=3–4 millimeters.

Therefore, $K=b/a=0.9$ $K'=b'/a'=0.9.$

Accordingly,

K=K'.

Hence, according to the broadest aspect of the present invention,

K≧K'.

Earpieces for universal use, rather than for the exclusive use of some specific people, should be elliptical or circular in cross sectional shape. The applicant is aware that the cross sectional shapes of ear canals are far more complex. However, any attempt at more closely approximating the cross sectional shapes of earpieces to those of ear canals would be unsuccessful. For such earpieces would better suit only a limited number of people, giving pain to others. The earpieces contoured and dimensioned in accordance with the foregoing teachings of the present invention will fit in the ear canals of the overwhelming majority of people. Although the wearer may feel some pressure in his external ear, he will feel hardly any pain at all despite a prolonged period of use.

Optionally, for higher wearing comfort, the rigidity or hardness of the canal insert 44 may be made higher at the part 66, FIG. 3, of its front portion 50 neighboring the concavity 54 than at the part 68 of the front portion 50 neighboring the convexity 56. Conversely, should the part 68 of the front portion 50 be made higher in rigidity, it would stimulate the sensitive cavity 38 in the ear canal, and the earpiece would become easier to undergo rotational displacement because of the presence of the more pliant part 66 of the front portion.

The hardness of silicone rubber or like earpiece materials according to the present invention may be 40 or more in JIS (Japanese Industrial Standards) hardness, preferably from 60 to 70. However, as has been ascertained by experiment, even materials with a JIS hardness of as high as 90 will hardly give any unpleasant sensation to all but a small number of people whose ear canals are exceptionally narrow.

Figure 7:
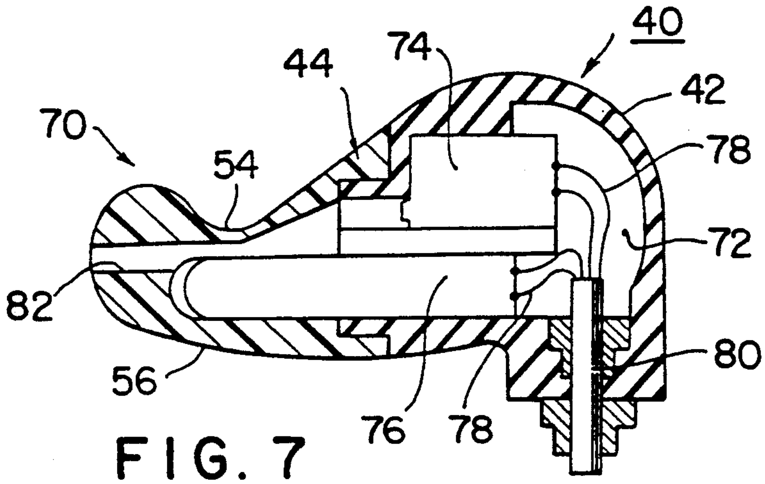
FIG. 7 is a section through an earphone/microphone combination including the earpiece of FIG. 3, the section being taken along the median plane of the earpiece.

Earphone/microphone Combination of FIG. 7

FIG. 7 shows the earpiece 40 of FIG. 3 as adapted for use as an earphone/microphone combination 70. The earpiece 40 has a hollow 72 formed in both its body part 42 and canal insert 44. Mounted in this earpiece hollow are an earphone transducer 74 and a microphone transducer 76, which are both electrically coupled to external equipment via leads 78 received in an insulating sheath and extending from within the earpiece as a flexible cord 80. The body part 42 and canal insert 44 of the earpiece 40 are pressfitted together after mounting the transducers 74 and 76 in the earpiece hollow 72. The canal insert 44 has a sound channel 82 communicating the earpiece hollow 72 with the ear canal.

This particular earphone/microphone combination 70 functions as microphone by utilizing the known biophysical principle of bone conduction, that is, the transmission of sound vibrations to the ear via the bones of the skull. Thus the microphone transducer 76 takes the form of a solid vibration pickup closely held against both body part 42 and canal insert 44 of the earpiece 40. The canal insert for use with the solid vibration pickup may be molded from silicone rubber with a JIS hardness of 70–80. The microphone transducer 76 will input the voice of the wearer by picking up the vibrations that have been transmitted to the external ear via the skull bones.

The earphone transducer 74, on the other hand, will translate the electric signal, supplied from the external equipment, into the audible vibrations of the air. Such air vibrations will travel through the sound channel 82 into the ear canal to strike the eardrum 12.

Since the earpiece 40 can be stably mounted in the ear canal, as has been discussed previously, the earphone/microphone combination 70 will not easily fall off even if the wearer makes rapid or violent movements. He will therefore be able to converse with someone at a distance while, for example, running or skiing.

The quality of the sound for transmission will generally be better if the canal insert 44, particularly its part 68, FIG. 3, is relatively hard. In case the canal insert 44 is of silicone rubber, that with a JIS hardness of 80–90 will make it possible for the microphone transducer 76 to better pick up the higher frequency component of the voice. Silicone rubber with a JIS hardness of 40–60 will result in the enhancement of sensitivity to a frequency range of 0.7–1.5 kilohertz. In this case, therefore, a microphone transducer may be employed that has a frequency characteristic complementary to that of the silicon rubber of that hardness range.

It is particularly recommended that the body part 42 of the earpiece 40 be made from elastic rubber or like material, and its canal insert 44 from a thermoplastic. The microphone transducer 76 will better pick up the higher frequency component of the voice, while being relatively insensitive to background noise, resulting in the transmission of clear speech.

Figure 8:
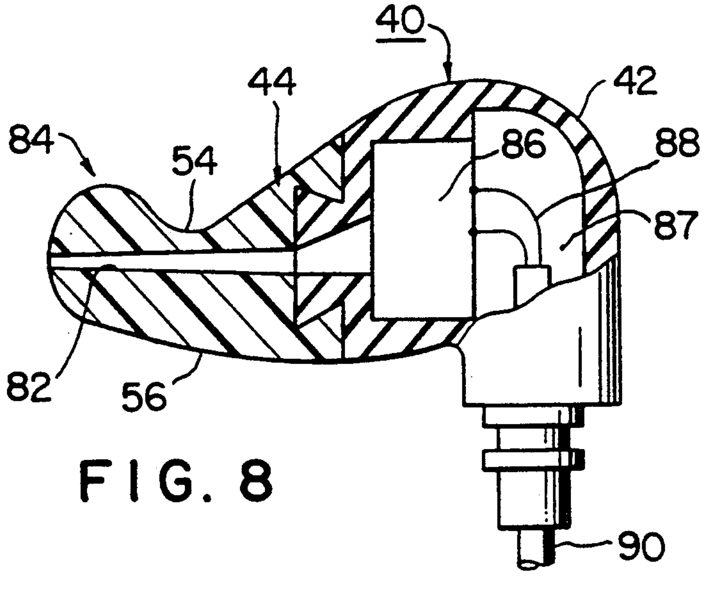
FIG. 8 is a similar section through an earphone including the earpiece of FIG. 3.

Earphone of FIG. 8

FIG. 8 is an illustration of an earphone 84 incorporating the FIG. 3 earpiece 40. The earphone 84 has only an earphone transducer 86 mounted in a hollow 87 in the body part 42 of the earpiece 40. The body part hollow 87 communicates with the ear canal through the channel 82 in the canal insert 44. The earphone transducer 86 has leads 88 extending outwardly from within the earpiece as a flexible cord 90 for electrical connection to external equipment.

Although of course incapable of sound transmission, this earphone 84 is well suited for applications where the wearer has to listen to distant speakers while moving. The earphone 84 will be put to the use of a greater number of people by molding its canal insert 44 from a pliant or elastic material or by using a spongy material for the part 68, FIG. 3, of the canal insert. However, the canal insert 44, or any local part of it, should not be so pliant that the earphone 84 will fall off the ear under its own weight. The cord 90 should be as pliant as practical in order to permit the earphone 84 to stay on the ear despite rapid movements of the wearer's head.

Figure 9:
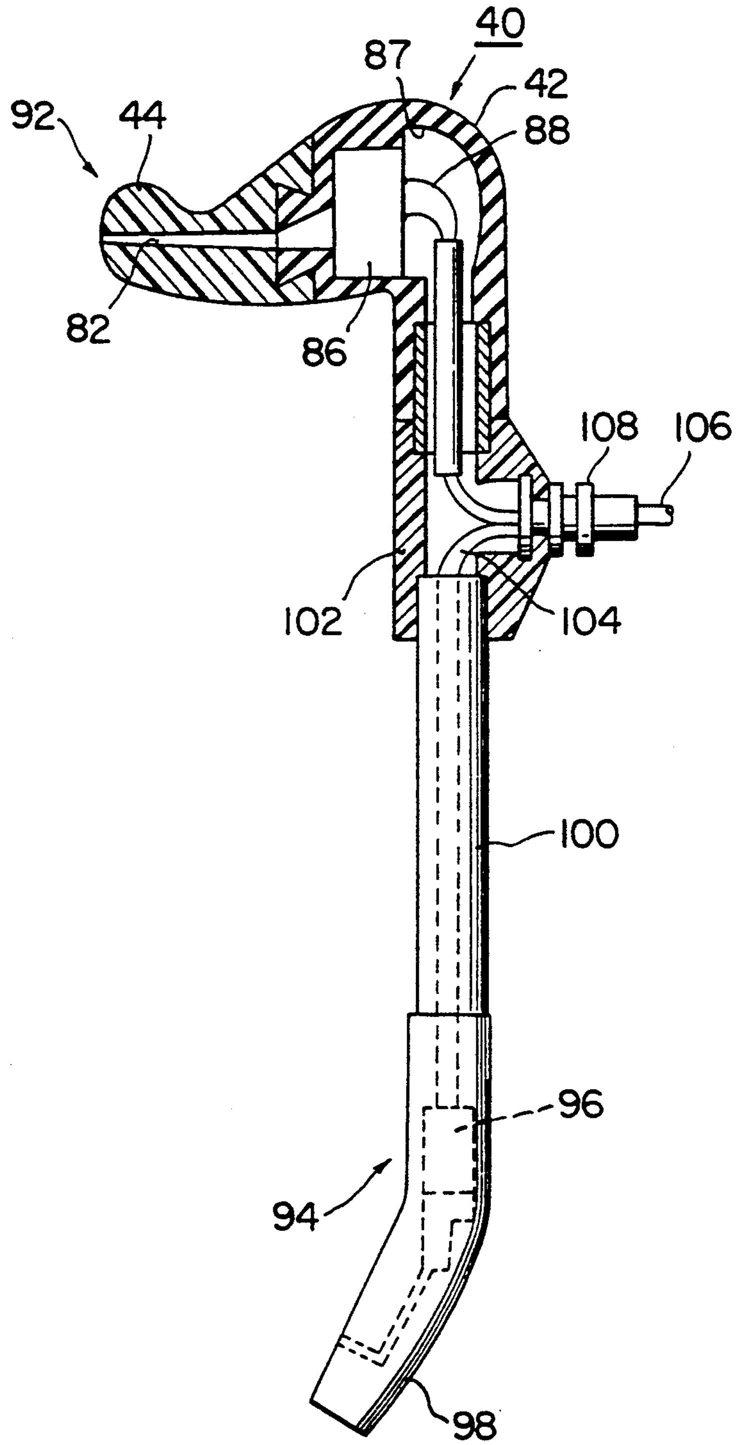
FIG. 9 is a combined sectional and elevational illustration of another example of earphone/microphone combination including the earpiece of FIG. 3.

Earphone/microphone Combination of FIG. 9

FIG. 9 shows another example of earphone/microphone combination 92 including the FIG. 3 earpiece 40. This earphone/microphone combination may be thought of as a combination of the FIG. 8 earphone 84 with a microphone assembly 94 coupled to the earpiece 40. The microphone assembly 94 comprises a microphone transducer 96 within a microphone enclosure 98, and a tubular sidepiece 100 connecting the microphone enclosure to the earpiece 40 via a molded plastic coupling 102. The microphone transducer 96 has leads 104 extending through the sidepiece 100. These microphone leads 104 are combined with the leads 88 of the earphone transducer 86 within the earpiece 40 into a flexible cord 106 extending through a fixture 108 affixed to the coupling 102. The cord 106 connects the earphone transducer 86 and microphone transducer 96 to external equipment.

In use of the earphone/microphone combination 92 the earpiece 40 may be inserted in the ear canal so as to hold the microphone transducer 96 close to the wearer's mouth. The microphone transducer 96 will then pick up the wearer's voice which has been transmitted thereto as audible vibrations of the air. The improved shape of the earpiece 40 according to the present invention makes it possible for the earphone/microphone combination 92 to be stably supported in position merely by inserting the earpiece in the ear canal, the total weight of the earphone/microphone combination being less than 20 grams.

Many suggestions have so far been made for earphone/microphone combinations. As far as the applicant is aware, however, they have all been in the form of a headphone or a headset, with a microphone connected thereto via a sidepiece. A drawback common to all such known devices is that they cannot possibly be mounted in position with one hand. The known headphones or headsets are also easy to fall off when the head is moved rapidly. Devices with ear hangers have also been proposed. However, being hung mostly over the helix of the pinna, they are totally ineffective when the wearer has to droop his or her head close to the ground or floor.

The earphone/microphone combination 92, including the earpiece 40 of improved shape, is free from all such weaknesses of the prior art. Thanks to the stability of the earpiece against angular displacement in the ear canal, the earphone/microphone combination can be firmly supported in position merely by the earpiece received in the ear canal, particularly if the total weight of the device is of the order of several tens of grams.

Figure 10:
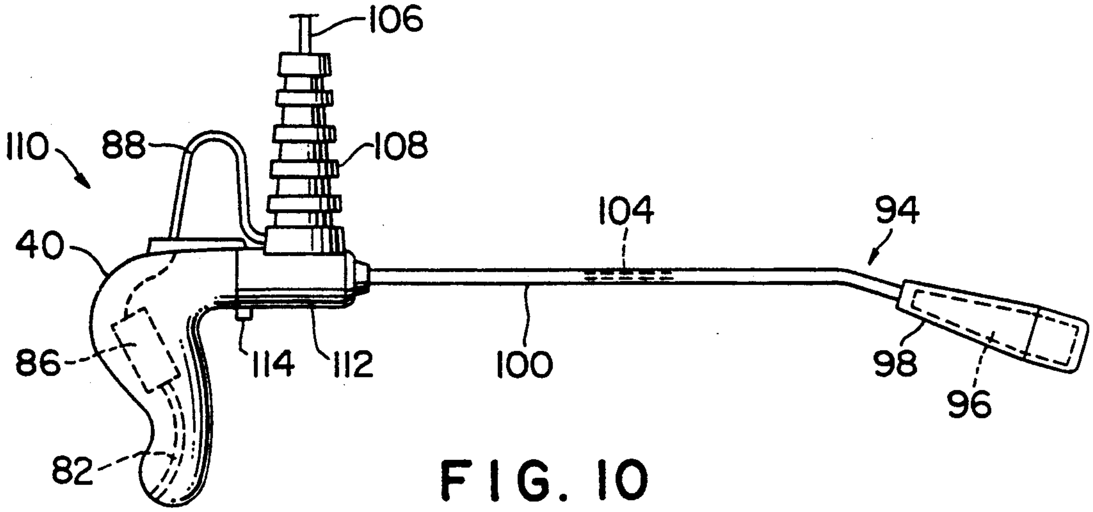
FIG. 10 is an elevation of still another example of earphone/microphone combination including the earpiece of FIG. 3.
Figure 11:
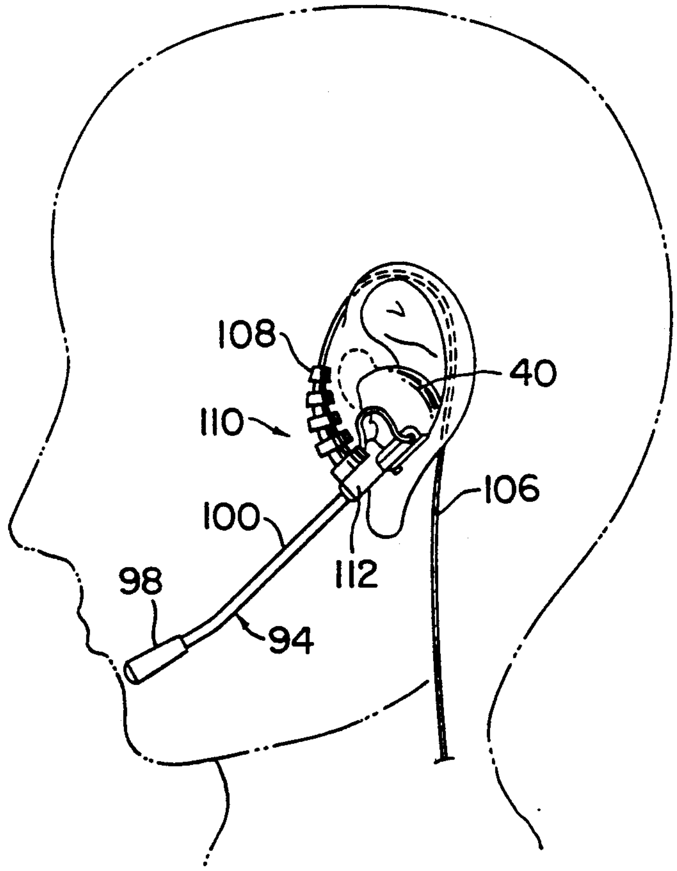
FIG. 11 is a pictorial illustration of how the earphone/microphone combination of FIG. 10 is mounted to the ear.

Earphone/microphone Combination of FIGS. 10–11

Still another earphone/microphone combination 110 shown in FIG. 10 is similar to the FIG. 9 earphone/microphone combination 92 but is explicitly designed to be readily mounted to either the left or the right ear. This earphone/microphone combination 110 also includes the FIG. 3 earpiece 40 housing the earphone transducer 86. The microphone transducer 96 within the enclosure 98 is supported on one end of the tubular sidepiece 100. This sidepiece is secured at the other end to a rotary coupling 112 attached to the earpiece 40. The rotary coupling 112, complete with a boss 114, is rotatable relative to the earpiece 40 through an angle of approximately three quarters of a complete revolution. The leads 88 of the earphone transducer 86 and the leads 104 of the microphone transducer 96 are combined into the single flexible cord 106 extending through the fixture 108 and connected to external equipment.

FIG. 11 is explanatory of a preferred mode of wearing the earphone/microphone combination 110. This figure shows the device mounted to the left ear. With the earpiece 40 inserted in the ear canal, the fixture 108 on the rotary coupling 112 is generally directed upwardly. The flexible cord 106 extending from the fixture 108 is then threaded over the pinna. This practice will serve to prevent the microphone assembly 94 from turning down under its own weight about the earpiece 40, holding the microphone transducer close to the wearer's mouth in spite of rapid movements of the head.

For mounting the earphone/microphone combination 110 to the right ear, the earpiece 40 may be inserted in the left ear canal. The rotary coupling 112 may then be revolved through a suitable angle relative to the earpiece 40 for directing the fixture upwardly, and the flexible cord 106 may be threaded over the right pinna.

Figure 12:
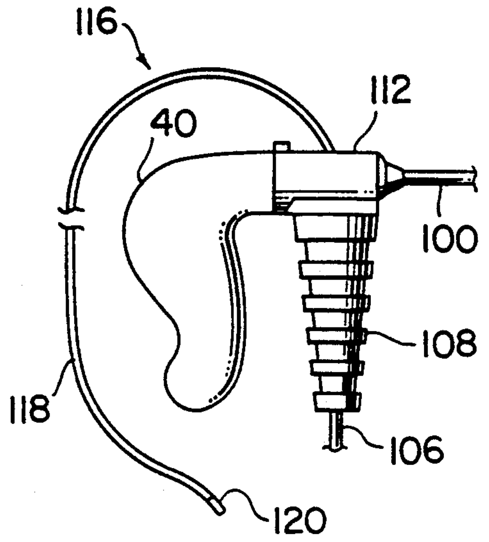
FIG. 12 is a partial elevation of a further example of earphone/microphone combination including the earpiece of FIG. 3.

Earphone/microphone Combination of FIG. 12

An earphone/microphone combination 116 shown in FIG. 12 differs from that of FIG. 10 only in having an ear hanger 118 in the form of a wire bent into the shape of a C to fit over the pinna. The ear hanger 118 is anchored at one end to the rotary coupling 112 and has another end formed into a hook 120.

The manner of use of the earphone/microphone combination 116 is similar to that of the FIG. 10 device 110, except that the ear hanger 118 instead of the cord 106 is engaged with the pinna. Further, after passing the ear hanger 118 over the pinna, the cord 106 may be manipulated into engagement with the terminal hook 120 of the ear hanger. The earphone/microphone combination 116 can thus be retained in position still more positively than the FIG. 10 device 110. This device 116 is also mountable to either the left or the right ear.

Figure 13:
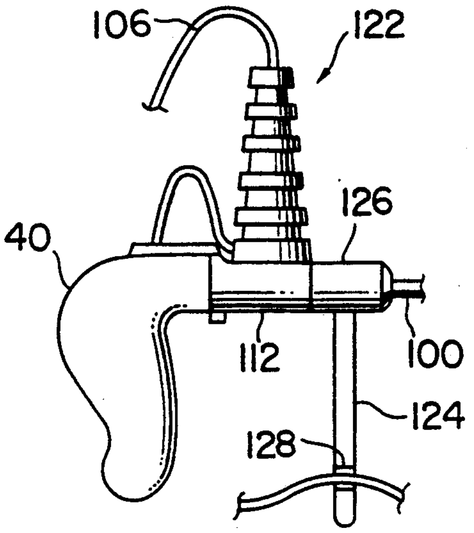
FIG. 13 is a partial elevation of a still further example of earphone/microphone including the earpiece of FIG. 3.
Figure 14:
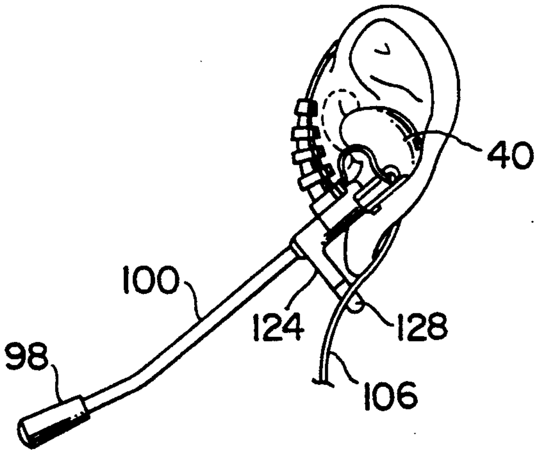
FIG. 14 is a pictorial illustration of how the earphone/microphone combination of FIG. 13 is mounted to the ear.

Earphone/microphone Combination of FIGS. 13-14

FIG. 13 illustrates another earphone/microphone combination 122 similar to that of FIG. 10. This earphone/microphone combination features a cord hook 124 in the form of a short rod anchored at one end to an extension 126 of the rotary coupling 112 and having a recess 128 for engaging the flexible cord 106. The other details of the earphone/microphone combination 122 are as set forth above with reference to FIG. 10.

The earphone/microphone combination 122 may be put to use as pictured in FIG. 14. It will be seen that, with the earpiece 40 inserted in the ear canal, the flexible cord 106 is threaded over the pinna and engaged in the recess 128 in the cord hook 124. This device 122 can therefore be retained in position nearly as positively as the FIG. 12 device 116. The mounting of the device 122 to the right ear is also possible.

The earpiece 40 set forth above with reference to FIGS. 3-6 is itself well designed to resist accidental detachment from, or angular displacement in, the ear canal to the maximum possible degree. However, in order to further enhance its stability in the ear canal, the earpiece may be provided with any of several different types of earpiece stabilizers disclosed hereafter. These earpiece stabilizers are adjustably mounted to the earpiece the concha, under some pressure. The contact stabilizers may be provided on both sides of the median plane of the earpiece, or on one side of the median plane if the resulting earpiece is for exclusive use with the right or left ear only.

Figure 15:
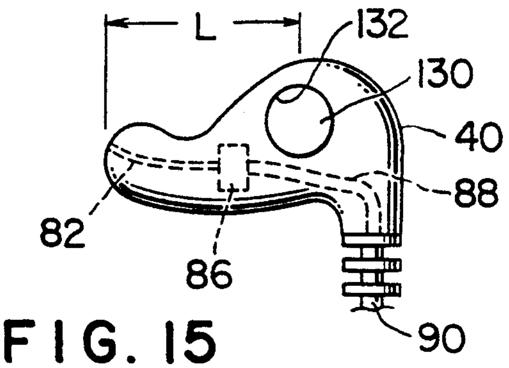
FIG. 15 is a side elevation of the earpiece of FIG. 3 provided with a preferred form of earpiece stabilizer according to the present invention, the earpiece being herein shown complete with an inbuilt earphone transducer for use as an earphone.
Figure 16:
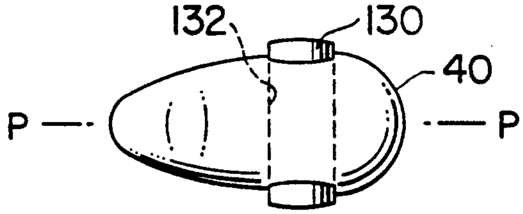
FIG. 16 is a top plan of the earpiece of FIG. 15.

Earpiece Stabilizer of FIGS. 15-16

FIGS. 15 and 16 show the earpiece stabilizer as a contact piece 130 in the form of a short rod or cylinder. The contact piece 130 slidably extends through a hole 132 formed in the earpiece 40 so as to extend perpendicular to the median plane P—P. The length of the contact piece 130 is greater than that of the hole 132, so that at least one end of the contact piece projects from the hole.

Preferably, the contact piece 130 is 6-10 millimeters in diameter and 16-23 millimeters in length. The distance L, FIG. 15, between the longitudinal axis of the contact piece 130 and the front tip of the canal insert of the earpiece 40 is 15-20 millimeters.

The position of the contact piece 130 on the earpiece 40 is such that one end of the contact piece, projecting from the hole 132, is to be received in the concha 20, FIGS. 1 and 2, when the earpiece is inserted in the ear canal 10. This projecting end of the contact piece 130 is to butt against the bottom wall of the concha or thereabouts, thereby positively holding the earpiece in the ear canal. The contact piece 130 may be pressed against the bottom wall of the concha by pushing the other end into the hole 132 after inserting the earpiece 40 in the ear canal. Which end of the contact piece 130 is to be pressed against the bottom wall of the concha depends, of course, upon which ear the earpiece is mounted to.

FIG. 15 further shows the earphone transducer 86 mounted within the earpiece 40, in a position away from the hole 132. The earphone transducer 86 has the leads 88 connected to external equipment by way of the flexible cord 90. The sound channel 82 extends forwardly from the earphone transducer 86 for communicating the same with the ear canal.

Figure 17:
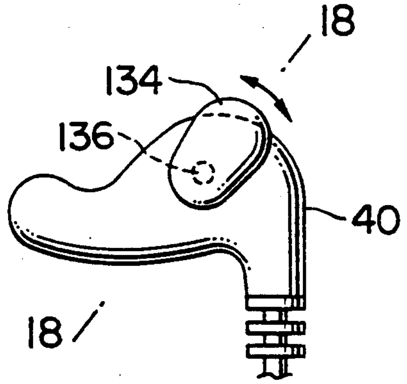
FIG. 17 is a view similar to FIG. 15 but showing the earpiece with another preferred form of stabilizer.
Figure 18:
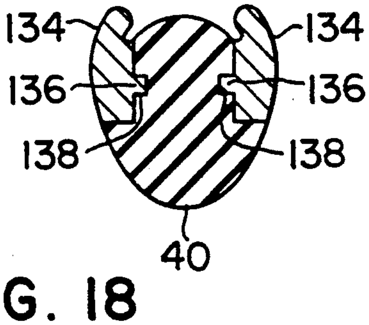
FIG. 18 is a section through the earpiece of FIG. 17, taken along the line 18—18 therein.

Earpiece Stabilizer of FIGS. 17-18

In FIGS. 17 and 18 the earpiece stabilizer is shown as a pair of contact pieces 134 pivotally mounted to the earpiece 40 in positions of symmetry with respect to its median plane. Each contact piece 134 is oval shaped, as seen in a side view as in FIG. 17, and has a small boss 136 projecting therefrom in a position off the geometrical center of the contact piece. The bosses 136 are rotatably engaged in holes 138 in the earpiece 40. With the pair of contact pieces 134 thus mounted in position on the earpiece 40, the maximum distance between the outer surfaces of the contact pieces may be approximately equal to the length of the contact piece 130 of FIGS. 15 and 16. The angular positions of the contact pieces 134 on the earpiece 40 may be adjusted, as indicated by the double headed arrow in FIG. 17, to the particular ear canal configuration of the wearer.

Figure 19:
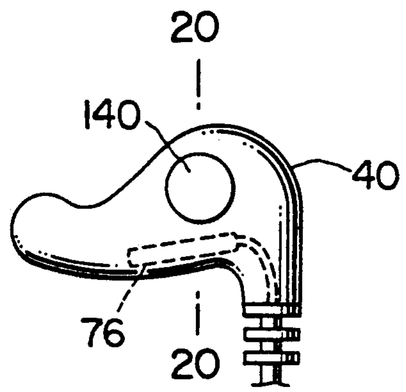
FIG. 19 is a view similar to FIG. 15 but showing the earpiece with still another preferred form of stabilizer, the earpiece being herein shown complete with an inbuilt solid vibration pickup for use as an ear microphone.
Figure 20:
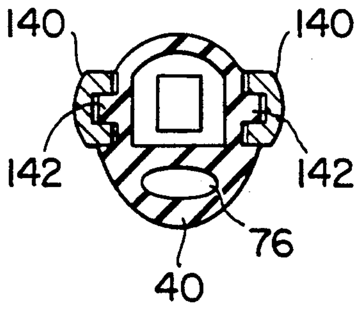
FIG. 20 is a section through the earpiece of FIG. 19, taken along the line 20—20 therein.

Earpiece Stabilizer of FIGS. 19-20

The earpiece stabilizer of FIGS. 19 and 20 comprises a pair of contact pieces 140 screw threadedly mounted to the earpiece 40 in positions of symmetry with respect to its median plane. Each contact piece 140 is shown as a short, hollow, internally threaded cylinder, open at one end and closed at another.

FIG. 20 shows that the earpiece 40 is formed to include a pair of threaded bosses 142 projecting therefrom. Engaged with these bosses 142, the pair of contact pieces 140 are aligned about an axis perpendicular to the median plane. Thus the contact pieces 140 may be individually turned in either a tightening or a loosening direction to an extent required to closely fit the earpiece to the particular ear canal of the wearer.

The earpiece 40 with the pair of contact pieces 140 thereon is further shown in FIGS. 19 and 20 as adapted for use as an ear mounted microphone, comprising the solid vibration pickup 76 built into the earpiece 40 as a microphone transducer. The solid vibration pickup 76 has been set forth in conjunction with the earphone/microphone transducer 70 of FIG. 7.

Figure 21:
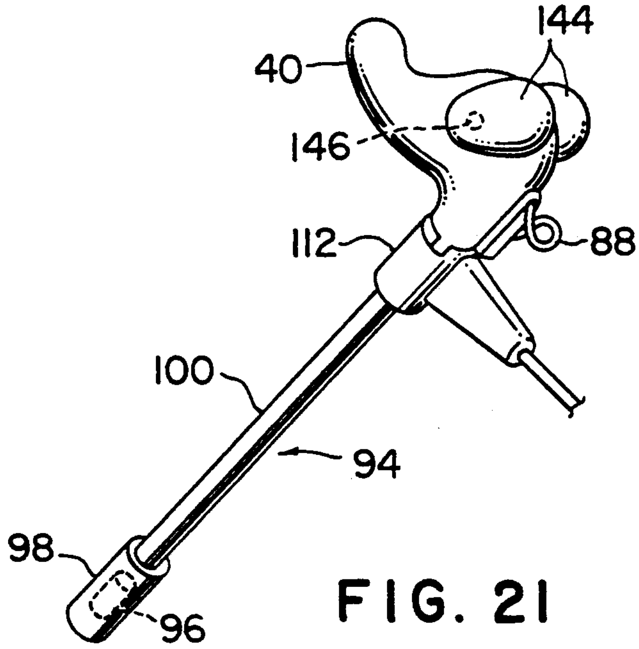
FIG. 21 is a perspective view of an earphone/microphone combination including the earpiece of FIG. 3 which is shown provided with a further preferred form of stabilizer.

Earpiece of FIG. 21

FIG. 21 shows a further preferred example of earpiece stabilizer comprising a pair of contact pieces 144, similar in shape to the contact pieces 134 of FIGS. 17 and 18, which are also mounted to the earpiece 40 in positions of symmetry with respect to its median plane. The contact pieces 144 are, however, mounted to the earpiece 40 by means of loosenable fastener elements such as screws 146.

Although not seen in FIG. 21, a plurality or multiplicity of interengageable ridges and furrows are understood to be formed on the mating surfaces of the earpiece 30 and contact pieces 144 in radial arrangement about the screws 146. Since the screws 146 are readily loosenable, the angular positions of the contact pieces 144 may be individually adjustable with respect to the earpiece 40 to suit the ear canal of the wearer. This embodiment offers the advantage that the contact pieces 144 can be positively retained in the required angular positions by retightening the screws 146.

The earpiece 40 with the pair of contact pieces 144 thereon is further shown adapted for use as an ear mounted microphone, comprising the microphone assembly 94 coupled to the earpiece via the rotary coupling 112. The microphone assembly 94 is similar in construction to that shown in FIGS. 9 and 10. The earpiece 40 may, or may not, have an earphone transducer mounted therein, although FIG. 21 shows the leads 88 of an earphone transducer extending from within the earpiece.

It is, of course, understood that the preferred embodiments of the present invention disclosed herein lend themselves to a variety of modifications, alterations, substitutions and omissions in order to conform to design preferences or to the requirements of each specific application of the invention. It is therefore appropriate that the present invention be construed broadly and in a manner consistent with the fair meaning or proper scope of the following claims.

What is claimed is:

1. An earpiece to be inserted in an ear canal as a part of an earphone, an ear mounted microphone, an earphone/microphone combination or the like, comprising:

(A) a body part;

(B) a canal insert joined to the body part and having a generally elongate shape to fit in an ear canal longitudinally thereof, the canal insert comprising:

(a) a rear portion joined directly to the body part;

(b) a front portion away from the body part, the front portion being of a substantially elliptical cross section; and (c) a midportion intermediate the rear portion and the front portion, the midportion being of a substantially elliptical cross section;

(d) there being a median plane with respect to which the canal insert is substantially of bilateral symmetry;

(e) said canal insert, when seen in a direction perpendicular to said median plane, having a concavity at the midportion along one side of the canal insert and being convexed along the other side of the canal insert, said concavity being shaped to fit on a prominence on the inner wall of the ear canal to prevent the earpiece from slipping out of the canal;

(f) there being the following dimensional relationship between the front portion and the midportion of the canal insert;

$$b/a > b'/a'$$

where a = the cross sectional dimension of the front portion of the canal insert as measured in a first direction which is perpendicular to the median plane;

b = the cross sectional dimension of the front portion of the canal insert as measured in a second direction which is contained in the median plane and which is at right angles with the first direction;

a' = the cross sectional dimension of the midportion of the canal insert as measured in a first direction;

b' = the cross sectional dimension of the midportion of the canal insert as measured in the second direction.

2. The earpiece of claim 1 wherein at least the canal insert is made from an elastic material.

3. The earpiece of claim 1 wherein at least the canal insert is made from silicone rubber.

4. The earpiece of claim 1 wherein the body part is made from an elastic material, and the canal insert from a thermoplastic.

5. The earpiece of claim 1 wherein the front portion of the canal insert has parts that differ from each other in hardness.

6. The earpiece of claim 1 further comprising an earpiece stabilizer movably mounted thereto on at least either side of the median plane for stabilizing the earpiece when the earpiece is inserted in the ear canal.

7. A earphone comprising:

(A) an earpiece to be inserted in an ear canal, the earpiece comprising a body part and a canal insert joined to the body part, the canal insert having a generally elongated shape to fit in an ear canal longitudinally thereof and comprising:

(a) a rear portion joined directly to the body part;

(b) a front portion away from the body part, the front portion being of a substantially elliptical cross section; and (c) a midportion intermediate the rear portion and the front portion, the midportion being of a substantially elliptical cross section;

(d) there being a median plane with respect to which the canal insert is substantially of bilateral symmetry;

(e) said canal insert, when seen in a direction perpendicular to said median plane, having a concavity at the midportion along one side of the canal insert and being convexed along the other side of the canal insert, said concavity being shaped to fit on a prominence on the inner wall of the ear canal to prevent the earpiece from slipping out of the canal;

(f) there being the following dimensional relationship between the front portion and the midportion of the canal insert;

$$b/a > b'/a'$$

where a = the cross sectional dimension of the front portion of the canal insert as measured in a first direction which is perpendicular to the median plane;

b = the cross sectional dimension of the front portion of the canal insert as measured in a second direction which is contained in the median plane and which is at right angles with the first direction;

a' = the cross sectional dimension of the midportion of the canal insert as measured in a first direction;

b' = the cross sectional dimension of the midportion of the canal insert as measured in the second direction; and (B) an earphone transducer built into the earpiece, there being a sound channel formed in the canal insert of the earpiece for communicating the earphone transducer with the ear canal.

8. An ear mounted microphone comprising:

(A) An earpiece to be inserted in an ear canal, the earpiece comprising a body part and a canal insert joined to the body part, the canal insert having a generally elongate shape to fit in an ear canal longitudinally thereof and comprising:

(a) a rear portion joined directly to the body part;
(b) a front portion away from the body part, the front portion being of a substantially ellipitcal cross section; and
(c) a midportion intermediate the rear portion and the front portion, the midportion being of a substantially elliptical cross section;
(d) there being a median plane with respect to which the canal insert is substantially of bilateral symmetry;
(e) said canal insert, when seen in a direction perpendicular to said median plane, having a concavity at the midportion along one side of the canal insert and being convexed along the other side of the canal insert, said concavity being shaped to fit on a prominence on the inner wall of the ear canal to prevent the earpiece from slipping out of the canal;
(f) there being the following dimensional relationship between the front portion and the midportion of the canal insert;

$$b/a>b'/a'$$

where a=the cross sectional dimension of the front portion of the canal insert as measured in a first direction which is perpendicular to the median plane;
b=the cross sectional dimension of the front portion of the canal insert as measured in a second direction which is contained in the median plane and which is at right angles with the first direction;
a'=the cross sectional dimension of the midportion of the canal insert as measured in a first direction;
b'=the cross sectional dimension of the midportion of the canal insert as measured in the second direction; and
(B) a vibration pickup built into the earpiece for picking up the voice of the wearer of the microphone.

9. An ear mounted microphone comprising:
An earpiece to be inserted in an ear canal, the earpiece comprising a body part and a canal insert joined to the body part, the canal insert having a generally elongate shape to fit in an ear canal longitudinally thereof and comprising:
(a) a rear portion joined directly to the body part;
(b) a front portion away from the body part, the front portion being of a substantially elliptical cross section; and
(c) a midportion intermediate the rear portion and the front portion, the midportion being at a substantially elliptical cross section;
(d) there being a median plane with respect to which the canal insert is substantially of bilateral symmetry;
(e) said canal insert, when seen in a direction perpendicular to said median plane, having a concavity at the midportion along one side of the canal insert and being convexed along the other side of the canal insert, said concavity being shaped to fit on a prominence on the inner wall of the ear canal to prevent the earpiece from slipping out of the canal:
(f) there being the following dimensional relationship between the front portion and the midportion of the canal insert;

$$b/a>b'/a'$$

where a=the cross sectional dimension of the front portion of the canal insert as measured in a first direction which is perpendicular to the median plane;
b=the cross sectional dimension of the front portion of the canal insert as measured in a second direction which is contained in the median plane and which is at right angles with the first direction;
a'=the cross sectional dimension of the midportion of the canal insert as measured in a first direction;
b'=the cross sectional dimension of the midportion of the canal insert as measured in the second direction; and
(B) a microphone assembly comprising:
(a) an elongate sidepiece having one end coupled to the earpiece; and
(b) a microphone transducer supported on an other end of the sidepiece.

10. The ear mounted microphone of claim 9 further comprising a rotary coupling connected between the earpiece and the sidepiece of the microphone assembly to permit rotation of the earpiece relative to the microphone assembly.

11. An earphone/microphone combination comprising:
(A) an earpiece to be inserted in an ear canal, the earpiece comprising a body part and a canal insert joined to the body part, the canal insert having a generally elongated shape to fit in an ear canal longitudinally thereof and comprising:
(a) a rear portion joined directly to the body part;
(b) a front portion away from the body part, the front portion being of a substantially elliptical cross section; and
(c) a midportion intermediate the rear portion and the front portion, the midportion being of a substantially elliptical cross section;
(d) there being a median plane with respect to which the canal insert is substantially of bilateral symmetry;
(e) said canal insert, when seen in a direction perpendicular to said median plane, having a concavity at the midportion along one side of the canal insert and being convexed along the other side of the canal insert, said concavity being shaped to fit on a prominence on the inner wall of the ear canal to prevent the earpiece from slipping out of the canal;
(f) there being the following dimensional relationship between the front portion and the midportion of the canal insert;

$$b/a>b'/a'$$

where a=the cross sectional dimension of the front portion of the canal insert as measured in a first direction which is perpendicular to the median plane;
b=the cross sectional dimension of the front portion of the canal insert as measured in a second direction which is contained in the median plane and which is at right angles with the first direction;
a'=the cross sectional dimension of the midportion of the canal insert as measured in a first direction;

b'=the cross sectional dimension of the midportion of the canal insert as measured in the second direction; and (B) an earphone transducer built into the earpiece, there being a sound channel formed in the canal insert of the earpiece for communicating the earphone transducer with the ear canal.

(C) a vibration pickup built into the earpiece for picking up the voice of the wearer of the microphone.

12. An earphone/microphone combination comprising:

(A) an earpiece to be inserted in an ear canal, the earpiece comprising a body part and a canal insert joined to the body part, the canal insert having a generally elongate shape to fit in an ear canal longitudinally thereof and comprising:

(a) a rear portion joined directly to the body part;

(b) a front portion away from the body part, the front portion being of a substantially elliptical cross section; and (c) a midportion intermediate the rear portion nd the front portion, the midportion being of a substantially elliptical cross section;

(d) there being a median plane with respect to which the canal insert is substantially of bilateral symmetry;

(e) said canal insert, when seen in a direction perpendicular to said median plane, having a concavity at the midportion along one side of the canal insert and being convexed along the other side of the canal insert, said concavity being shaped to fit on a prominence on the inner wall of the ear canal to prevent the earpiece from slipping out of the canal;

(f) there being the following dimensional relationship between the front portion and the midportion of the canal insert;

$$b/a > b'/a'$$

where a=the cross sectional dimension of the front portion of the canal insert as measured in a first direction which is perpendicular to the median plane;

b=the cross sectional dimension of the front portion of the canal insert as measured in a second direction which is contained in the median plane and which is at right angles with the first direction;

a'=the cross sectional dimension of the midportion of the canal insert as measured in a first direction;

b'=the cross sectional dimension of the midportion of the canal insert as measured in the second direction;

(B) an earphone transducer built into the earpiece, there being a sound channel formed in the canal insert of the earpiece for communicating the earphone transducer with the ear canal; and (C) a microphone transducer supported on another end of the sidepiece.

13. The earphone/microphone combination of claim 12 further comprising an ear hanger coupled to the earpiece.

14. The earphone/microphone combination of claim 12 further comprising a rotary coupling connected between the earpiece and the sidepiece of the microphone assembly to permit rotation of the earpiece relative to the microphone assembly.

15. The earphone/microphone combination of claim 14 further comprising:

(a) a cord extending through the rotary coupling for electrically connecting the earphone transducer and the microphone transducer to external equipment; and (b) an ear hanger having one end anchored to the rotary coupling and another end hooked for engaging the cord.

16. The earphone/microphone combination of claim 14 further comprising:

(a) a cord extending through the rotary coupling for electrically connecting the earphone transducer and the microphone transducer to external equipment; and (b) a cord hook coupled to the rotary coupling for engaging the cord.

17. An earpiece to be inserted in an ear canal as a part of an earphone, an ear mounted microphone, an ear phone/microphone combination or the like, comprising:

(A) a body part;

(B) a canal insert joined to the body part and having a generally elongate shape to fit in an ear canal, the canal insert comprising:

(a) a rear portion joined directly to the body part;

(b) a front portion away from the body part; and (c) a midportion intermediate the rear portion and the front portion;

(d) there being a median plane with respect to which the canal insert is substantially of bilateral symmetry;

(e) there being the following dimensional relationship between the front portion and the midportion of the canal insert;

$$b/a \geqq b'/b'$$

where a=the cross sectional dimension of the front portion of the canal insert as measured in a first direction which is perpendicular to the median plane;

b=the cross sectional dimension of the front portion of the canal insert as measured in a second direction which is contained in the median plane and which is at right angles with the first direction;

a'=the cross sectional dimension of the midportion of the canal insert as measured in a first direction;

b'=the cross sectional dimension of the midportion of the canal insert as measured in the second direction; and (C) an earpiece stabilizer movably mounted to the earpiece on at least either side of the median plane for stabilizing the earpiece when the earpiece is inserted in the ear canal, said earpiece stabilizer comprising a contact piece in the form of a rod slidably received in a hole extending through the earpiece in a direction perpendicular to the median plane, the contact piece having at least one end projecting from the hole.

18. An earpiece to be inserted in an ear canal as a part of an earphone, an ear mounted microphone, an ear phone/microphone combination or the like, comprising:

(A) a body part;

(B) a canal insert joined to the body part and having a generally elongate shape to fit in an ear canal, the canal insert comprising:
(a) a rear portion joined directly to the body part;
(b) a front portion away from the body part; and
(c) a midportion intermediate the rear portion and the front portion;
(d) there being a median plane with respect to which the canal insert is substantially of bilateral symmetry;
(e) there being the following dimensional relationship between the front portion and the midportion of the canal insert;

$$b/a \geqq b'/a'$$

where
a=the cross sectional dimension of the front portion of the canal insert as measured in a first direction which is perpendicular to the median plane;
b=the cross sectional dimension of the front portion of the canal insert as measured in a second direction which is contained in the median plane and which is at right angles with the first direction;
a'=the cross sectional dimension of the midportion of the canal insert as measured in a first direction;
b'=the cross sectional dimension of the midportion of the canal insert as measured in the second direction; and
(C) an earpiece stabilizer movably mounted to the earpiece on at least either side of the median plane for stabilizing the earpiece when the earpiece is inserted in the ear canal, said earpiece stabilizer comprising a pair of contact pieces pivotally mounted to the earpiece on the opposite sides of the median plane.

19. An earpiece to be inserted in an ear canal as a part of an earphone, an ear mounted microphone, an ear phone/microphone combination or the like, comprising:
(A) a body part;
(B) a canal insert joined to the body part and having a generally elongated shape to fit in an ear canal, the canal insert comprising:
(a) a rear portion joined directly to the body part;
(b) a front portion away from the body part; and
(c) a midportion intermediate the rear portion and the front portion;
(d) there being a median plane with respect to which the canal insert is substantially of bilateral symmetry;
(e) there being the following dimensional relationship between the front portion and the midportion of the canal insert;

$$b/a \geqq b'/a'$$

where
a=the cross sectional dimension of the front portion of the canal insert as measured in a first direction which is perpendicular to the median plane;
b=the cross sectional dimension of the front portion of the canal insert as measured in a second direction which is contained in the median plane and which is at right angles with the first direction;
a'=the cross sectional dimension of the midportion of the canal insert as measured in a first direction;
b'=the cross sectional dimension of the midportion of the canal insert as measured in the second direction; and
(C) an earpiece stabilizer movably mounted to the earpiece on at least either side of the median plane for stabilizing the earpiece when the earpiece is inserted in the ear canal, said earpiece stabilizer comprising a pair of contact pieces screw threadedly mounted to the earpiece on the opposite sides of the medianplane.

20. An earpiece to be inserted in an ear canal as a part of an earphone, an ear mounted microphone, an ear phone/microphone combination or the like, comprising:
(A) a body part;
(B) a canal insert joined to the body part and having a generally elongate shape to fit in an ear canal, the canal insert comprising:
(a) a rear portion joined directly to the body part;
(b) a front portion away from the body part; and
(c) a midportion intermediate the rear portion and the front portion;
(d) there being a medina plane with respect to which the canal insert is substantially of bilateral symmetry;
(e) there being the following dimensional relationship between the front portion and the midportion of the canal insert;

$$b/a \geqq b'/a'$$

a=the cross sectional dimension of the front portion of the canal insert as measured in a first direction which is perpendicular to the median plane;
b=the cross sectional dimension of the front portion of the canal insert as measured in a second direction which is contained in the median plane and which is at right angles with the first direction;
a'=the cross sectional dimension of the midportion of the canal insert as measured in a first direction;
b'=the cross sectional dimension of the midportion of the canal insert as measured in the second direction; and
(C) an earpiece stabilizer movably mounted to the earpiece on at least either side of the median plane for stabilizing the earpiece when the earpiece is inserted in the ear canal, said earpiece stabilizer comprising a pair of contact pieces mounted by means of loosenable fastener elements to the earpiece on the opposite sides of the median plane, so that the angular positions of the contact pieces about the fastener elements are adjustably variable by loosening the fastener elements.

21. The earpiece of claim 18 wherein the pair of contact pieces are each oval shaped as seen in a direction perpendicular to the median plane.

22. The earpiece of claim 19 wherein the pair of contact pieces are each in the form of a hollow, internally screw threaded cylinder, closed at one end and open at another end.

23. The earpiece of claim 20 wherein the pair of contact pieces are each oval shaped as seen in a direction perpendicular to the median plane.

* * * * *